(12) United States Patent
Vanderlinde et al.

(10) Patent No.: US 6,957,100 B2
(45) Date of Patent: Oct. 18, 2005

(54) METHOD AND SYSTEM FOR DISPLAY OF CARDIAC EVENT INTERVALS IN A RESYNCHRONIZATION PACEMAKER

(75) Inventors: Scott Vanderlinde, Plymouth, MN (US); Jeffrey E. Stahmann, Ramsey, MN (US); Rene H. Wentkowski, White Bear Lake, MN (US); David Ternes, Roseville, MN (US); James Kalgren, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/748,724

(22) Filed: Dec. 26, 2000

(65) Prior Publication Data

US 2002/0082509 A1 Jun. 27, 2002

(51) Int. Cl.⁷ .................................................. A61B 5/04
(52) U.S. Cl. ...................................... 600/510; 600/523
(58) Field of Search ............................... 600/504, 510, 600/519, 523; 607/4–7, 91, 14–15, 17–18, 25–32, 122–123, 148

(56) References Cited

U.S. PATENT DOCUMENTS

| | | | |
|---|---|---|---|
| 3,857,399 A | 12/1974 | Zacouto | 128/419 P |
| 4,030,510 A | 6/1977 | Bowers | 128/419 PG |
| 4,059,116 A | 11/1977 | Adams | 128/419 PG |

(Continued)

FOREIGN PATENT DOCUMENTS

| | | | |
|---|---|---|---|
| EP | 0033418 | 12/1980 | A61N/1/36 |
| EP | 0360412 | 3/1990 | A61N/1/365 |
| EP | 0401962 | 12/1990 | A61N/1/368 |
| EP | 0597459 | 5/1994 | A61N/1/39 |
| EP | 0617980 | 10/1994 | A61N/1/368 |
| EP | 0748638 | 12/1996 | A61N/1/368 |
| WO | WO-93/02746 | 2/1993 | A61N/1/368 |
| WO | WO-95/092029 | 4/1995 | |
| WO | WO-9711745 | 4/1997 | A61N/1/362 |
| WO | WO-98/48891 | 11/1998 | A61N/1/362 |
| WO | WO-00/71200 | 11/2000 | A61N/1/362 |
| WO | WO-00/71202 | 11/2000 | A61N/1/362 |
| WO | WO-00/71203 | 11/2000 | A61N/1/39 |

OTHER PUBLICATIONS

U.S. Appl. No. 09/316,588, filed May 21, 1999, 6,285,907, System Providing Ventricular Pacing and Biventricular Coordination.

U.S. Appl. No. 09/837,019, filed Apr. 18, 2001, 6,411,848, System Providing Ventricular Pacing and Biventricular Coordination.

U.S. Appl. No. 09/615,588, filed Jul. 13, 2000, 6,424,865, Ventricular Conduction Delay Trending System and Method.

U.S. Appl. No. 09/579,951, filed May 26, 2000, 6,501,987, Rate Smoothing Control.

U.S. Appl. No. 09/748,358, filed Dec. 26, 2000, 6,501,988, Apparatus and Method for Ventricular Rate Regularization With Biventricular Sensing.

U.S. Appl. No. 09/751,431, filed Dec. 29, 2000, Apparatus and Method for Ventricular Rate Regularization.

(Continued)

Primary Examiner—Mark Bockelman
(74) Attorney, Agent, or Firm—Schwegman, Lundberg, Woessner & Kluth, P.A.

(57) ABSTRACT

A cardiac rhythm management system that includes a pacemaker configured for biventricular pacing and an external programmer with an associated display for displaying electrogram data and markers representing ventricular events. Associated with each marker are intraventricular intervals designed to relate information to a user in a manner suited for ventricular resynchronization pacing.

14 Claims, 2 Drawing Sheets

U.S. PATENT DOCUMENTS

| | | | |
|---|---|---|---|
| 4,163,451 A | 8/1979 | Lesnick et al. | 128/419 PG |
| 4,208,008 A | 6/1980 | Smith | 371/15 |
| RE30,387 E | 8/1980 | Denniston, III et al. | 126/419 |
| 4,432,360 A | 2/1984 | Mumford et al. | 128/419 PG |
| 4,503,857 A | 3/1985 | Boute et al. | 128/419 PG |
| 4,556,063 A | 12/1985 | Thompson et al. | 128/419 PT |
| 4,562,841 A | 1/1986 | Brockway et al. | 128/419 PG |
| 4,596,255 A | 6/1986 | Snell et al. | 128/697 |
| 4,791,936 A | 12/1988 | Snell et al. | 128/697 |
| 4,809,697 A | 3/1989 | Causey, III et al. | 128/419 PT |
| 4,830,006 A | 5/1989 | Haluska et al. | 607/4 |
| 4,869,252 A | 9/1989 | Gilli | 128/419 PG |
| 4,890,617 A | 1/1990 | Markowitz et al. | 128/419 PG |
| 4,905,697 A | 3/1990 | Heggs et al. | 128/419 PG |
| 4,917,115 A | 4/1990 | Flammang et al. | 128/419 PG |
| 4,920,965 A | 5/1990 | Funke et al. | 128/419 PG |
| 4,928,688 A | 5/1990 | Mower | 128/419 PG |
| 4,940,054 A | 7/1990 | Grevis et al. | 128/419 PG |
| 4,941,471 A | 7/1990 | Mehra | 128/419 |
| 4,944,298 A | 7/1990 | Sholder | 128/419 PG |
| 4,944,928 A | 7/1990 | Grill et al. | 423/161 |
| 4,945,909 A | 8/1990 | Fearnot et al. | 128/419 PG |
| 4,972,834 A | 11/1990 | Begemann et al. | 128/419 |
| 4,998,974 A | 3/1991 | Aker | 128/419 PG |
| 5,012,814 A | 5/1991 | Mills et al. | 128/691 |
| 5,042,480 A | 8/1991 | Hedin et al. | 128/419 PG |
| 5,085,215 A | 2/1992 | Nappholz et al. | 128/419 PG |
| 5,101,824 A | 4/1992 | Lekholm | 128/419 PG |
| 5,107,850 A | 4/1992 | Olive | 128/705 |
| 5,127,404 A | 7/1992 | Wyborny et al. | 128/419 P |
| 5,129,394 A | 7/1992 | Mehra | 128/419 PG |
| 5,139,020 A | 8/1992 | Koestner et al. | 128/419 PG |
| 5,144,949 A | 9/1992 | Olson | 128/419 PG |
| 5,156,147 A | 10/1992 | Warren et al. | 128/419 PG |
| 5,156,154 A | 10/1992 | Valenta, Jr. et al. | 128/661.09 |
| 5,179,949 A | 1/1993 | Chirife | 128/419 PG |
| 5,183,040 A | 2/1993 | Nappholz et al. | 128/419 PG |
| 5,184,614 A | 2/1993 | Collins et al. | 128/419 PG |
| 5,188,106 A | 2/1993 | Nappholz et al. | 128/419 PG |
| 5,193,535 A | 3/1993 | Bardy et al. | 128/419 D |
| 5,193,550 A | 3/1993 | Duffin | 128/697 |
| 5,197,467 A | 3/1993 | Steinhaus et al. | 128/419 PG |
| 5,207,219 A | 5/1993 | Adams et al. | 128/419 D |
| 5,282,836 A | 2/1994 | Kreyenhagen et al. | 607/4 |
| 5,284,491 A | 2/1994 | Sutton et al. | 607/17 |
| 5,292,339 A | 3/1994 | Stephens et al. | 607/15 |
| 5,292,341 A | 3/1994 | Snell | 607/30 |
| 5,311,874 A | 5/1994 | Baumann et al. | 128/705 |
| 5,312,452 A | 5/1994 | Salo | 607/17 |
| 5,331,966 A | 7/1994 | Bennett et al. | 128/696 |
| 5,334,220 A | 8/1994 | Sholder | 607/9 |
| 5,350,409 A | 9/1994 | Stoop et al. | 607/17 |
| 5,356,425 A | 10/1994 | Bardy et al. | 607/14 |
| 5,360,437 A | 11/1994 | Thompson | 607/30 |
| 5,365,932 A | 11/1994 | Greenhut | 128/698 |
| 5,379,776 A | 1/1995 | Murphy et al. | 128/705 |
| 5,383,910 A | 1/1995 | den Dulk | 607/14 |
| 5,387,229 A | 2/1995 | Poore | 607/18 |
| 5,391,189 A | 2/1995 | van Krieken et al. | 607/17 |
| 5,395,373 A | 3/1995 | Ayers | 607/8 |
| 5,395,397 A | 3/1995 | Lindgren et al. | 607/9 |
| 5,400,796 A | 3/1995 | Wecke | 128/705 |
| 5,411,524 A | 5/1995 | Rahul | 607/4 |
| 5,411,531 A | 5/1995 | Hill et al. | 607/14 |
| 5,417,714 A | 5/1995 | Levine et al. | 607/9 |
| 5,423,869 A | 6/1995 | Poore et al. | 607/18 |
| 5,431,691 A | 7/1995 | Snell et al. | 607/27 |
| 5,437,285 A | 8/1995 | Verrier et al. | 128/702 |
| 5,462,060 A | 10/1995 | Jacobson et al. | 128/702 |
| 5,474,574 A | 12/1995 | Payne et al. | 607/7 |
| 5,480,413 A | 1/1996 | Greenhut et al. | 607/14 |
| 5,486,198 A | 1/1996 | Ayers et al. | 607/5 |
| 5,487,752 A | 1/1996 | Salo et al. | 607/17 |
| 5,507,782 A | 4/1996 | Kieval et al. | 607/9 |
| 5,507,784 A | 4/1996 | Hill et al. | 607/14 |
| 5,514,163 A | 5/1996 | Markowitz et al. | 607/9 |
| 5,522,850 A | 6/1996 | Yomtov et al. | 607/5 |
| 5,522,859 A | 6/1996 | Stroebel et al. | 607/19 |
| 5,523,942 A | 6/1996 | Tyler et al. | 354/401 |
| 5,527,347 A | 6/1996 | Shelton et al. | 607/9 |
| 5,534,016 A | 7/1996 | Boute | 607/9 |
| 5,540,232 A | 7/1996 | Laney et al. | 128/697 |
| 5,540,727 A | 7/1996 | Tockman et al. | 607/18 |
| 5,545,182 A | 8/1996 | Stotts et al. | 607/5 |
| 5,545,186 A | 8/1996 | Olson et al. | 607/14 |
| 5,549,649 A | 8/1996 | Florio et al. | 607/15 |
| 5,549,654 A | 8/1996 | Powell | 607/32 |
| 5,554,174 A | 9/1996 | Causey, III | 607/6 |
| 5,560,369 A | 10/1996 | McClure et al. | 128/704 |
| 5,560,370 A | 10/1996 | Verrier et al. | 128/705 |
| 5,584,864 A | 12/1996 | White | 607/5 |
| 5,584,867 A | 12/1996 | Limousin et al. | 607/9 |
| 5,591,215 A | 1/1997 | Greenhut et al. | 607/14 |
| 5,605,159 A | 2/1997 | Smith et al. | 128/702 |
| 5,607,460 A | 3/1997 | Kroll et al. | 607/30 |
| 5,613,495 A | 3/1997 | Mills et al. | 128/696 |
| 5,620,471 A | 4/1997 | Duncan | 607/14 |
| 5,620,473 A | 4/1997 | Poore | 607/27 |
| 5,622,178 A | 4/1997 | Gilham | 128/696 |
| 5,626,620 A | 5/1997 | Kieval et al. | 607/9 |
| 5,626,622 A | 5/1997 | Cooper | 607/18 |
| 5,626,623 A | 5/1997 | Kieval et al. | 607/23 |
| 5,632,267 A | 5/1997 | Hognelid et al. | 607/5 |
| 5,674,250 A | 10/1997 | de Coriolis et al. | 607/7 |
| 5,674,251 A | 10/1997 | Combs et al. | 607/4 |
| 5,674,255 A | 10/1997 | Walmsley et al. | 607/14 |
| 5,676,153 A | 10/1997 | Smith et al. | 128/702 |
| 5,683,429 A | 11/1997 | Mehra | 602/14 |
| 5,690,689 A | 11/1997 | Sholder | 607/24 |
| 5,700,283 A | 12/1997 | Salo | 607/17 |
| 5,713,929 A | 2/1998 | Hess et al. | 607/14 |
| 5,713,930 A | 2/1998 | van der Veen et al. | 607/25 |
| 5,713,932 A | 2/1998 | Gillberg et al. | 607/27 |
| 5,716,382 A | 2/1998 | Snell | 607/30 |
| 5,716,383 A | 2/1998 | Kieval et al. | 607/9 |
| 5,716,384 A | 2/1998 | Snell | 607/30 |
| 5,718,235 A | 2/1998 | Golosarsky et al. | 128/708 |
| 5,724,985 A | 3/1998 | Snell et al. | 128/697 |
| 5,725,559 A | 3/1998 | Alt et al. | 607/5 |
| 5,725,561 A | 3/1998 | Stroebel et al. | 607/9 |
| 5,730,141 A | 3/1998 | Fain et al. | 128/705 |
| 5,730,142 A | 3/1998 | Sun et al. | 128/705 |
| 5,738,096 A | 4/1998 | Ben-Haim | 128/653.1 |
| 5,741,304 A | 4/1998 | Patwardhan et al. | 607/5 |
| 5,741,308 A | 4/1998 | Sholder | 607/9 |
| 5,749,901 A | 5/1998 | Bush et al. | 607/5 |
| 5,749,906 A | 5/1998 | Kieval et al. | 607/9 |
| 5,755,736 A | 5/1998 | Gillberg et al. | 607/4 |
| 5,755,737 A | 5/1998 | Prieve et al. | 607/4 |
| 5,755,739 A | 5/1998 | Sun et al. | 607/14 |
| 5,755,740 A | 5/1998 | Nappholz | 607/18 |
| 5,759,196 A | 6/1998 | Hess et al. | 607/14 |
| 5,776,164 A | 7/1998 | Ripart | 607/5 |
| 5,776,167 A | 7/1998 | Levine et al. | 607/9 |
| 5,782,183 A | 7/1998 | Andrews, Jr. | 607/14 |
| 5,782,887 A | 7/1998 | Van Krieken et al. | 607/25 |
| 5,788,717 A | 8/1998 | Mann et al. | 607/14 |
| 5,800,464 A | 9/1998 | Kieval | 607/9 |
| 5,800,471 A | 9/1998 | Baumann | 607/25 |
| 5,814,077 A | 9/1998 | Sholder et al. | 607/9 |
| 5,814,081 A | 9/1998 | Ayers et al. | 607/5 |

| | | | |
|---|---|---|---|
| 5,814,085 A | 9/1998 | Hill | 607/14 |
| 5,836,975 A | 11/1998 | DeGroot | 607/5 |
| 5,836,987 A | 11/1998 | Baumann et al. | 607/17 |
| 5,840,079 A | 11/1998 | Warman et al. | 607/4 |
| 5,842,997 A | 12/1998 | Verrier et al. | 600/518 |
| 5,846,263 A | 12/1998 | Peterson et al. | 607/14 |
| 5,853,426 A | 12/1998 | Shieh | 607/5 |
| 5,855,593 A | 1/1999 | Olson et al. | 607/9 |
| 5,861,007 A | 1/1999 | Hess et al. | 607/9 |
| 5,865,838 A | 2/1999 | Obel et al. | 607/5 |
| 5,873,895 A | 2/1999 | Sholder et al. | 607/9 |
| 5,873,897 A | 2/1999 | Armstrong et al. | 607/14 |
| 5,891,178 A | 4/1999 | Mann et al. | 607/27 |
| 5,893,882 A | 4/1999 | Peterson et al. | 607/14 |
| 5,897,575 A | 4/1999 | Wickham | 607/4 |
| 5,902,324 A | 5/1999 | Thompson et al. | 607/9 |
| 5,928,271 A | 7/1999 | Hess et al. | 607/14 |
| 5,931,857 A | 8/1999 | Prieve et al. | 607/14 |
| 5,935,081 A | 8/1999 | Kadhiresan | 600/513 |
| 5,944,744 A | 8/1999 | Paul et al. | 607/9 |
| 5,951,592 A | 9/1999 | Murphy | 607/4 |
| 5,968,079 A | 10/1999 | Warman et al. | 607/5 |
| 5,974,341 A | 10/1999 | Er et al. | 607/31 |
| 5,978,707 A | 11/1999 | Krig et al. | 607/14 |
| 5,978,710 A | 11/1999 | Prutchi et al. | 607/17 |
| 5,983,138 A | 11/1999 | Kramer | 607/9 |
| 5,987,354 A | 11/1999 | Cooper et al. | 607/5 |
| 5,987,356 A | 11/1999 | DeGroot | 607/5 |
| 5,991,656 A | 11/1999 | Olson et al. | 607/4 |
| 5,991,657 A | 11/1999 | Kim | 607/5 |
| 5,991,662 A | 11/1999 | Kim et al. | 607/27 |
| 5,999,850 A | 12/1999 | Dawson et al. | 607/4 |
| 6,026,320 A | 2/2000 | Carlson et al. | 600/510 |
| 6,041,251 A | 3/2000 | Kim et al. | 600/518 |
| 6,044,298 A | 3/2000 | Salo et al. | 607/17 |
| 6,047,210 A | 4/2000 | Kim et al. | 607/4 |
| 6,049,735 A | 4/2000 | Hartley et al. | 607/9 |
| 6,052,617 A | 4/2000 | Kim | 600/518 |
| 6,052,620 A | 4/2000 | Gillberg et al. | 607/4 |
| 6,058,328 A | 5/2000 | Levine et al. | 607/14 |
| 6,081,745 A | 6/2000 | Mehra | 607/4 |
| 6,081,746 A | 6/2000 | Pendekanti et al. | 607/5 |
| 6,081,747 A | 6/2000 | Levine et al. | 607/9 |
| RE36,765 E | 7/2000 | Mehra | 607/4 |
| 6,085,116 A | 7/2000 | Pendekanti et al. | 607/5 |
| 6,088,618 A | 7/2000 | Kerver | 607/30 |
| 6,091,988 A | 7/2000 | Warman et al. | 607/5 |
| 6,096,064 A | 8/2000 | Routh | 607/9 |
| 6,122,545 A | 9/2000 | Struble et al. | 607/9 |
| 6,151,524 A | 11/2000 | Krig et al. | 607/14 |
| 6,223,072 B1 | 4/2001 | Mika et al. | 600/510 |
| 6,246,909 B1 | 6/2001 | Ekwall | 607/9 |
| 6,249,699 B1 | 6/2001 | Kim | 607/4 |
| 6,256,534 B1 | 7/2001 | Dahl | 607/5 |
| 6,263,242 B1 | 7/2001 | Mika et al. | 607/9 |
| 6,266,554 B1 | 7/2001 | Hsu et al. | 600/515 |
| 6,272,380 B1 | 8/2001 | Warman et al. | 607/5 |
| 6,285,907 B1 | 9/2001 | Kramer et al. | 607/9 |
| 6,317,632 B1 | 11/2001 | Krig et al. | 607/14 |
| 6,353,759 B1 | 3/2002 | Hartley et al. | 607/9 |
| 6,408,209 B1 | 6/2002 | Bouhour et al. | 607/19 |
| 6,411,847 B1 | 6/2002 | Mower | 607/9 |
| 6,411,848 B2 | 6/2002 | Kramer et al. | 607/9 |
| 6,424,865 B1 | 7/2002 | Ding | 607/9 |
| 6,430,438 B1 | 8/2002 | Chen et al. | 607/5 |
| 6,434,424 B1 | 8/2002 | Igel et al. | 607/9 |
| 6,438,410 B2 | 8/2002 | Hsu et al. | 600/516 |
| 6,501,987 B1 | 12/2002 | Lovett et al. | 607/9 |
| 6,501,988 B2 | 12/2002 | Kramer et al. | 607/9 |
| 6,512,951 B1 | 1/2003 | Marcovecchio et al. | 607/5 |
| 6,522,925 B1 | 2/2003 | Gilkerson et al. | |
| RE38,119 E | 5/2003 | Mower | 607/9 |
| 6,763,267 B2 | 7/2004 | Ding | |
| 6,847,842 B1 | 1/2005 | Rodenhiser et al. | |
| 2002/0082660 A1 | 6/2002 | Stahmann et al. | |
| 2002/0087198 A1 | 7/2002 | Kramer et al. | |
| 2002/0091415 A1 | 7/2002 | Lovett et al. | |
| 2003/0069610 A1 | 4/2003 | Kramer et al. | |
| 2003/0078630 A1 | 4/2003 | Lovett et al. | |
| 2003/0233131 A1 | 12/2003 | Kamer et al. | |
| 2004/0010295 A1 | 1/2004 | Kramer et al. | |
| 2004/0172076 A1 | 9/2004 | Stahmann et al. | |
| 2004/0215259 A1 | 10/2004 | Krig et al. | |
| 2004/0243188 A1 | 12/2004 | Vanderlinde et al. | |
| 2005/0038480 A1 | 2/2005 | Ding | |

OTHER PUBLICATIONS

U.S. Appl. No. 09/792,651, filed Feb. 23, 2001, Apparatus and Method for Ventricular Rate Regularization.

U.S. Appl. No. 10/713,556, filed Nov. 13, 2003, Apparatus and Method For Pacing Mode Switching During Atrial Tachyarrhythmias.

U.S. Appl. No. 10/792,663, filed Mar. 3, 2004, Method and System For Display of Cardiac Event Intervals in a Resynchronization Pacemaker.

U.S. Appl. No. 10/852,602, filed May 24, 2004, Method and Apparatus for Treating Irregular Ventricular Contractions Such as During Atrial Arrhythmia.

U.S. Appl. No. 10/889,354, filed Jul. 12, 2004, Ventricular Conduction Delay Trending System and Method.

*Metrix Model 3020 Implantable Atrial Defibrillator*, Physician's Manual, InControl, Inc., Redmond, WA,(1998),pp. 4-24-4-27.

"French CNH Equipment Approvals", *Clinica 417, p. 9*, (Sep. 5, 1990),3 pages.

"Pacemaker System Guide for PULSAR MAX II; Multiprogrammable pacemakers", Product brochure published by Guidant Corporation,(Apr. 18, 1999),pp. 6-48-6-49, "Pacemaker System Guide for PULSAR MAX II; Multiprogrammable Pacemakers", Product brochure published by Guident Corporation,(1999),p. 6-39-6-51.

"Rate-Adaptive Devices Impact Pacemaker Market", *Clinica, 467, p. 16*, (Sep. 11, 1991),6 pages.

"Vitratron Medical Harmony Automatic Dual Chamber Pacemaker Product Information and Programming Guide ", Product Brochure published by Vitatron Medical,(Date Unknown),22 pgs.

Ayers, Gregory M., et al., "Venticular Proarrhythmic Effects of Ventricular Cycle Length and Shock Strength in a Sheep Model of Transvenous Atrial Defibrillation", *Circulation, 89 (1)*, (Jan, 1994),pp. 413-422.

Blommaert, D., et al., "Effective Prevention of Atrial Fibrillation by Continuous Artial Overdrive Pacing After Coronary Artery Bypass Surgery", *JACC, vol. 35, No. 6*, (May 2000), pp. 1411-1415.

Campbell, R. M., et al., "Artial Overdrive Pacing for Conversion of Artial Flutter in Children", *Pediatrics, vol. 75, No. 4*, (Apr. 1985),pp. 730-736.

Duckers, H. J., et al., "Effective use of a novel rate-smoothing algorithm in atrial fibrillation by ventricular pacing", *European Heart Journal, 18*, (1997),pp. 1951-1955.

Fahy, G. J., et al., "Pacing Strategies to Prevent Atrial Fibrillation", *Atrial Fibrillation, 14 (4)*, (Nov. 1996),pp. 591-596.

Fromer, M., et al., "Algorithm for the Prevention of Ventricular Tachycardia Onset: The Prevent Study", *The American Journal of Cardiology, 83 (5B)*, (Mar. 11, 1999),pp. 45D–47D.

Garrigue, S., et al., "Prevention of Artial Arrhythmias during DDD Pacing by Atrial Overdrive", *PACE, vol. 21*, (Sep. 1998),pp. 1751–1759.

Huer, H., et al., "Dynamic Dual–Chamber Overdrive Pacing with an Implantable Pacemaker System: A New Method for Terminating Slow Venticular Tachycardia", *Zeitschrift fur Kardiologie, 75*, German Translation by the Ralph McElroy Translation Company, Austin, TX,(1986),5 p.

Huer, H., et al., "Dynamische Zweikammer–Overdrive–Stimulation mit einem implantierbaren Schrittmachersystem als neue Methode zur Beendigung Langsamer ventrikularer Tachykardien", *Z Kardiol; 75*, Includes English translation (5 pgs.),(1986),pp. 673–675.

Jenkins, et al., "Diagnosis of Atrial Fibrillation Using Electrogram from Chronic Leads: Evaluation of Computer Algorithm", *PACE, 11*, (1988),pp. 622–631.

Jung, J., et al., "Discrimination of Sinus Rhythm, Artial Flutter and Atrial Fibrillation Using Bipolar Endocardial Signals", *Journal of Cardiovascular Electrophysiology, 9 (7)*, (Jul. 1998),pp. 689–695.

Morris, et al., "Intracardiac Electrogram Transformation: Morphometric Implications for Implantable Devices", *Journal of Electrocardiology, 29 Supplement*, (1996),pp. 124–129.

Murgatroyd, F. D., et al., "A New Pacing Algorithm for Overdrive Suppression of Atrial Fibrillation", *Pace, vol. 17.*, (Nov. 1994, Part),pp. 1966–1973.

Schuller, et al., "Far Field R–Wave Sensing—An Old Problem Repeating", *PACE, 19, Part II*, NASPE Abstract No. 264,(1996),p. 631.

Seim, G., et al., "Classification of Artial Flutter and Atrial Fibrillation Using an Atrial Dispersion Index (ADI)", *Guidant CRM Therapy Research Peer Review Report Revision 2.0*, (Jan. 6, 1999),27 p.

Stephany, et al., "Real–Time Estimation of Magnitude–Square Coherence for Use in Implantable Devices", *IEEE Computers in Cardiology*, (1992),pp. 375–378.

Sutton, R., "Pacing in Atrial Arrhymias", *PACE, vol. 13*, (Dec. 1990, Part),pp. 1823–1827

Swiryn, S., et al., "Detection of Atrial Fibrillation by Pacemakers and Antiarrhythmic Devices", *Nonpharmacological Management of Atrial Fibrillation, Chapter 21*, Futura Publishing Co, Inc. Armonk, NY,(1997),pp. 309–318.

Zhu, D. W., "Electrophysiology, Pacing and Arrhythmia", *Clin. Cardiol., vol. 19*, (Sep. 1996),pp. 737–742.

Buhr, Trina A., et al., "Novel Pacemaker Algorithm Diminishes Short–Coupled Ventricular Beats in Atrial Fibrillation", *PACE, vol. 24, Part II*, (Apr. 2001),729.

Greenhut, S., et al., "Effectiveness of a Ventricular Rate Stabilization Algorithm During Atrial Fibrillation in Dogs", *Pace Abstract*, Abstract No. 60,(1996),1 p.

Lau, Chu–Pak, et al., "Efficacy of Ventricular Rate Stabilization by Right Ventricular Pacing During Atrial Fibrillation", *PACE, vol. 21*, (Mar. 1998),542–548.

Mehra, R., et al., "Prevention of Artial Fibrillation/Flutter by Pacing Techniques", *Interventional Electrophysiology, Second Edition*, Chapter 34, Futura Publishing Company, Inc., (1996),pp. 521–540.

Wittkampf, Fred H., et al., "Effect of Right Venticular Pacing on Ventricular Rhythm During Atrial Fibrillation", *JACC, vol. 11 No. 3*, (Mar. 1988),539–545.

Wittkampf, F.H.M. et al., "Rate Stabililization by Right Venticular Pacing in Patients with Artial Fibrillation", *Pace, vol. 9, Part II*, (Nov.–Dec. 1986),1147–1153.

Guidant, "Contak TR CHFD Model 1241", *System Guide*, Congestive Heart Failure Device,(1999),1–191.

Hartley, Jesse W., et al., "Method and Apparatus For Treating Irregular Ventricular Contractions Such As During Atrial Arryhthmia", *U.S. Appl. No. 09/315,515, filed May 21, 1999*.

Lovett Eric, "Cardiac Pacing Systerm For Prevention of Ventricular Fibrillation and Ventricular Tachycardia Episode", *U.S. Appl. No. 09/569,295, filed May 13, 2000*, 71 pages.

Medtronic, "INSYNC III Device Model 8042", *Device Programming Guide*, INSYNC III Device Model 8042, Vision Programmer Software Model 9981, (2000), 1–260.

Medtronic, "INSYNC III Device Model 8042", *Device Reference Guide*, INSYNC III Device Model 8042, Vision Programmer Software Model 9981, (2002), 1–252.

St. Jude Medical, "Atlas + HF Models V–343, V–341", *User's Manual*, Implantable Cardioverter–Defibrillator, (Sep. 2003), 1–30.

St. Jude Medical, "Epic Hf Model V–339", *User's Manual*, Implantable Cardioverter–Defibrillator, (Jul. 2002), 1–26.

St. Jude Medical, "Model 3510 Programmer with Model 3307 Software", *Reference Manual*, For Atlas, Atlas+, Epic, Epic+, Photo u and Photon Implantable Cardioverter/Defibrillators, (Sep. 2003),1–314.

METHOD AND SYSTEM FOR DISPLAY OF CARDIAC EVENT INTERVALS IN A RESYNCHRONIZATION PACEMAKER

FIELD OF THE INVENTION

This invention pertains to cardiac rhythm management devices such as pacemakers. In particular, the invention relates to methods and systems for the display of data collected by such devices.

BACKGROUND

Cardiac pacemakers are cardiac rhythm management devices that provide electrical stimulation in the form of pacing pulses to selected chambers of the heart. (As the term is used herein, a pacemaker is any cardiac rhythm management device that performs cardiac pacing, including implantable cardioverter/defibrillators having a pacing functionality.) Cardiac rhythm management devices are usually implanted subcutaneously on a patient's chest and have leads threaded intravenously into the heart to connect the device to electrodes used for sensing and pacing, the electrodes being disposed in proximity to selected chambers of the heart. Pacemakers typically have a programmable electronic controller that causes the pacing pulses to be output in response to lapsed time intervals and sensed intrinsic cardiac activity.

The most common condition for which pacemakers are used is in the treatment of bradycardia, where the ventricular rate is too slow. If functioning properly, a pacemaker makes up for the heart's inability to pace itself at an appropriate rhythm in order to meet metabolic demand by enforcing a minimum heart rate. Pacing therapy can also be used in the treatment of congestive heart failure (CHF). It has also been shown that some CHF patients suffer from intraventricular and/or interventricular conduction defects such that their cardiac outputs can be increased by improving the synchronization of right and left ventricular contractions with electrical stimulation, referred to herein as ventricular resynchronization therapy.

Modern pacemakers also typically have the capability to communicate data via a data link with an external programming device. Such data is transmitted to the pacemaker in order to program its mode of operation as well as define other operating parameters. Data is also transmitted from the pacemaker which can be used to verify the operating parameters as well as inform the clinician as to the condition of both the pacemaker and the patient. Among the most useful data which may typically be telemetered from the pacemaker are electrograms representing the time sequence of sensing and pacing events. The present invention is concerned with informatively displaying such electrogram data.

SUMMARY OF THE INVENTION

The present invention relates to a method and system for displaying time intervals between cardiac events on an external programmer display based upon data transmitted from a pacemaker operating in a resynchronization pacing mode. In such a mode, one heart chamber may be designated as a rate chamber with the contralateral chamber designated as the synchronized chamber. Sensing/pacing channels are provided for each chamber, and one or both of the chambers are paced in a mode based upon senses and paces occurring in the rate chamber. For example, in a biventricular resynchronization pacing mode, paces may be output synchronously to either both ventricles or only one ventricle based upon right ventricular senses. In accordance with the invention, markers representing cardiac sensing and pacing events are displayed spaced apart in accordance with their time sequence. Each marker indicates whether the event is a sense or a pace and in which chamber the event occurred. Associated with each marker is also an indication of a intraventricular interval for the event, which is the time interval measured from another ventricular event.

In one embodiment, where the pacemaker is operating in a biventricular resynchronization pacing mode based upon right ventricular senses, markers for both right and left ventricular events are displayed with time intervals measured from the previous right ventricular event. In the case of a left ventricle-only pacing mode, right and left ventricular event markers are displayed with time intervals measured from the nearest preceding right ventricular sense or left ventricular pace. In another embodiment for biventricular resynchronization pacing, left ventricular event markers are displayed with time intervals measured from the nearest right ventricular event, which may precede or follow the left ventricular event marker as indicated by the interval being positive or negative, respectively. In a modification to this embodiment, the absolute value of the interval is displayed in alignment with the marker representing the later of either the left ventricular or right ventricular event.

DESCRIPTION OF THE INVENTION

It is useful for a clinician to be able to monitor the operation of a pacemaker with an external programmer by viewing a representation of an electrogram indicating a temporal sequence of sensing and pacing events. In a pacemaker configured to pace either ventricle or both ventricles in order to deliver ventricular resynchronization therapy, events occurring in both the right and left ventricular sensing/pacing channels should be displayed. Such a pacemaker may pace the heart in a number of different pacing modes, including modes in which one ventricle is paced based upon senses in the other ventricle. The present invention is a scheme for presenting this information along with time intervals between ventricular events in a clear and concise manner across the different pacing modes that the pacemaker may employ.

1. Hardware Platform

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
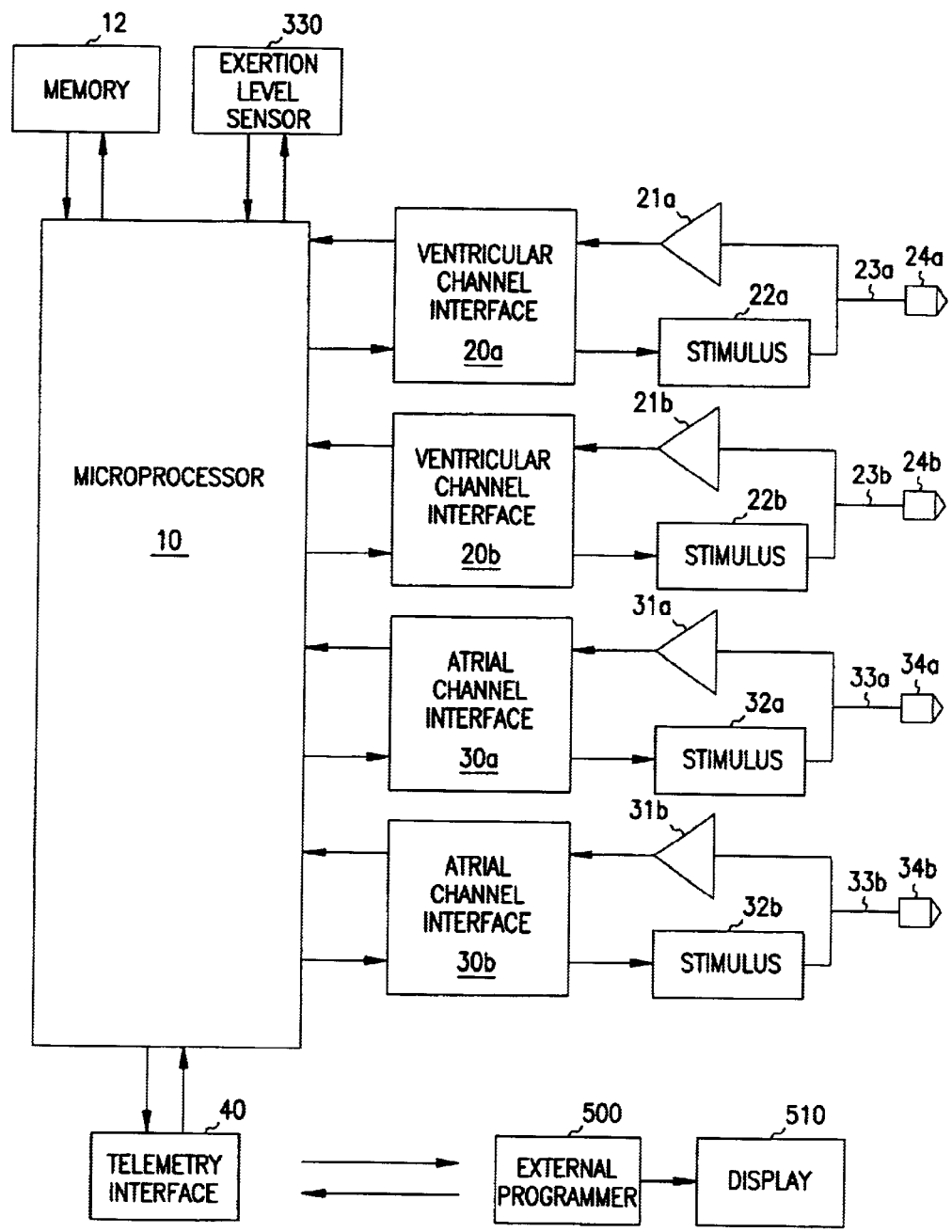
FIG. 1 is a system diagram of a cardiac rhythm management system that includes a microprocessor-based pacemaker and external programmer.

FIG. 1 shows a system diagram of a microprocessor-based pacemaker physically configured with sensing and pacing channels for both atria and both ventricles. The controller 10 of the pacemaker is a microprocessor which communicates with a memory 12 via a bidirectional data bus. The memory 12 typically comprises a ROM (read-only memory) for program storage and a RAM (random-access memory) for data storage. The pacemaker has atrial sensing and pacing channels comprising electrode 34a–b, leads 33a–b, sensing amplifiers 31a–b, pulse generators 32a–b, and atrial channel interfaces 30a–b which communicate bidirectionally with microprocessor 10. The device also has ventricular sensing and pacing channels for both ventricles comprising electrodes 24a–b, leads 23a–b, sensing amplifiers 21a–b, pulse generators 22a–b, and ventricular channel interfaces 20a–b. In the figure, "a" designates one ventricular or atrial channel and "b" designates the channel for the contralateral chamber. In this embodiment, a single electrode is used for sensing and pacing in each channel, known as a unipolar lead. Other embodiments may employ bipolar leads which include two electrodes for outputting a pacing pulse and/or sensing intrinsic activity. The channel interfaces 20a–b and 30a–b include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 (e.g., an accelerometer or a minute ventilation sensor) enables the controller to adapt the pacing rate in accordance with changes in the patient's physical activity. A telemetry interface 40 is also provided for communicating with an external programmer 500 which has an associated display 510. A pacemaker incorporating the present invention may possess all of the components in FIG. 1 and be programmable so as to operate in a number of different modes, or it may have only those components necessary to operate in a particular mode.

The controller 10 controls the overall operation of the device in accordance with programmed instructions stored in memory. The controller 10 interprets sense signals from the sensing channels and controls the delivery of paces in accordance with a pacing mode. The sensing circuitry of the pacemaker generates atrial and ventricular sense signals when voltages sensed by the electrodes exceed a specified threshold. The sense signals from each channel, together with the paces delivered, represent an electrogram that can either be transmitted via the telemetry link to an external programmer or stored for later transmission. The operation of the pacemaker and the patient's cardiac activity may thus be observed in real-time or over a selected historical period. In the latter case, the recording of an electrogram may be triggered by the detection of certain events or conditions such as an arrhythmia.

2. Bradycardia Pacing Modes

Bradycardia pacing modes refer to pacing algorithms used to pace the atria and/or ventricles when the intrinsic atrial and/or ventricular rate is inadequate due to, for example, AV conduction blocks or sinus node dysfunction. Such modes may either be single-chamber pacing, where either an atrium or a ventricle is paced, or dual-chamber pacing in which both an atrium and a ventricle are paced. The modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modern pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrioventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate limit interval is then the sum of the atrial escape interval and the atrio-ventricular interval.

Another type of synchronous pacing is atrial-triggered or ventricular-triggered pacing. In this mode, an atrium or ventricle is paced immediately after an intrinsic beat is detected in the respective chamber. Triggered pacing of a heart chamber is normally combined with inhibited demand pacing so that a pace is also delivered upon expiration of an escape interval in which no intrinsic beat occurs. Such triggered pacing may be employed as a safer alternative to asynchronous pacing when, due to far-field sensing of electromagnetic interference from external sources or skeletal muscle, false inhibition of pacing pulses is a problem. If a sense in the chamber's sensing channel is an actual depolarization and not a far-field sense, the triggered pace is delivered during the chamber's physiological refractory period and is of no consequence.

Finally, rate-adaptive algorithms may be used in conjunction with bradycardia pacing modes. Rate-adaptive pacemakers modulate the ventricular and/or atrial escape intervals based upon measurements corresponding to physical activity. Such pacemakers are applicable to situations in which atrial tracking modes cannot be used. In a rate-adaptive pacemaker operating in a ventricular pacing mode, for example, the LRL is adjusted in accordance with exertion level measurements such as from an accelerometer or minute ventilation sensor in order for the heart rate to more nearly match metabolic demand. The adjusted LRL is then termed the sensor-indicated rate.

3. Cardiac Resynchronization Therapy

Cardiac resynchronization therapy is pacing stimulation applied to one or more heart chambers in a manner that restores or maintains synchronized bilateral contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. In that sense, conventional bradycardia pacing of an atrium and/or a ventricle may be considered as resynchronization therapy. Resynchronization pacing, however, may also involve pacing both ventricles and/or both atria in accordance with a synchronized pacing mode as described below. A single chamber may also be resynchronized to compensate for intra-atrail or intra-ventricular conduction delays by delivering paces to multiple sites of the chamber.

It is advantageous to deliver resynchronization therapy in conjunction with one or more synchronous bradycardia pacing modes, such as are described above. One atrial and/or one ventricular pacing sites are designated as rate sites, and paces are delivered to the rate sites based upon pacing and sensed intrinsic activity at the site in accordance with the bradycardia pacing mode. In a single-chamber bradycardia pacing mode, for example, one of the paired atria or one of the ventricles is designated as the rate chamber. In a dual-chamber bradycardia pacing mode, either the right or left atrium is selected as the atrial rate chamber and either the right or left ventricle is selected as the ventricular rate chamber. The heart rate and the escape intervals for the pacing mode are defined by intervals between sensed and paced events in the rate chambers only. Resynchronization therapy may then be implemented by adding synchronized pacing to the bradycardia pacing mode where paces are delivered to one or more synchronized pacing sites in a defined time relation to one or more selected sensing and pacing events that either reset escape intervals or trigger paces in the bradycardia pacing mode. Multiple synchronized sites may be paced through multiple synchronized sensing/pacing channels, and the multiple synchronized sites may be in the same or different chambers as the rate site.

In bilateral synchronized pacing, which may be either biatrial or biventricular synchronized pacing, the heart chamber contralateral to the rate chamber is designated as a synchronized chamber. For example, the right ventricle may be designated as the rate ventricle and the left ventricle designated as the synchronized ventricle, and the paired atria may be similarly designated. Each synchronized chamber is then paced in a timed relation to a pace or sense occurring in the contralateral rate chamber.

One synchronized pacing mode may be termed offset synchronized pacing. In this mode, the synchronized chamber is paced with a positive, negative, or zero timing offset as measured from a pace delivered to its paired rate chamber, referred to as the synchronized chamber offset interval. The offset interval may be zero in order to pace both chambers simultaneously, positive in order to pace the synchronized chamber after the rate chamber, or negative to pace the synchronized chamber before the rate chamber. One example of such pacing is biventricular offset synchronized pacing where both ventricles are paced with a specified offset interval. The rate ventricle is paced in accordance with a synchronous bradycardia mode which may include atrial tracking, and the ventricular escape interval is reset with either a pace or a sense in the rate ventricle. (Resetting in this context refers to restarting the interval in the case of an LRL ventricular escape interval and to stopping the interval in the case of an AVI.) Thus, a pair of ventricular paces are delivered after expiration of the AVI escape interval or expiration of the LRL escape interval, with ventricular pacing inhibited by a sense in the rate ventricle that restarts the LRL escape interval and stops the AVI escape interval. In this mode, the pumping efficiency of the heart will be increased in some patients by simultaneous pacing of the ventricles with an offset of zero. However, it may be desirable in certain patients to pace one ventricle before the other in order to compensate for different conduction velocities in the two ventricles, and this may be accomplished by specifying a particular positive or negative ventricular offset interval.

Another synchronized mode is triggered synchronized pacing. In one type of triggered synchronized pacing, the synchronized chamber is paced after a specified trigger interval following a sense in the rate chamber, while in another type the rate chamber is paced after a specified trigger interval following a sense in the synchronized chamber. The two types may also be employed simultaneously. For example, with a trigger interval of zero, pacing of one chamber is triggered to occur in the shortest time possible after a sense in the other chamber in order to produce a coordinated contraction. (The shortest possible time for the triggered pace is limited by a sense-to-pace latency period dictated by the hardware.) This mode of pacing may be desirable when the intra-chamber conduction time is long enough that the pacemaker is able to reliably insert a pace before depolarization from one chamber reaches the other. Triggered synchronized pacing can also be combined with offset synchronized pacing such that both chambers are paced with the specified offset interval if no intrinsic activity is sensed in the rate chamber and a pace to the rate chamber is not otherwise delivered as a result of a triggering event. A specific example of this mode is ventricular triggered synchronized pacing where the rate and synchronized chambers are the right and left ventricles, respectively, and a sense in the right ventricle triggers a pace to the left ventricle and/or a sense in the left ventricle triggers a pace to the right ventricle.

As with other synchronized pacing modes, the rate chamber in a triggered synchronized pacing mode can be paced with one or more synchronous bradycardia pacing modes. If the rate chamber is controlled by a triggered bradycardia mode, a sense in the rate chamber sensing channel, in addition to triggering a pace to the synchronized chamber, also triggers an immediate rate chamber pace and resets any rate chamber escape interval. The advantage of this modal combination is that the sensed event in the rate chamber sensing channel might actually be a far-field sense from the synchronized chamber, in which case the rate chamber pace should not be inhibited. In a specific example, the right and left ventricles are the rate and synchronized chambers, respectively, and a sense in the right ventricle triggers a pace to the left ventricle. If right ventricular triggered pacing is also employed as a bradycardia mode, both ventricles are paced after a right ventricular sense has been received to allow for the possibility that the right ventricular sense was actually a far-field sense of left ventricular depolarization in the right ventricular channel. If the right ventricular sense were actually from the right ventricle, the right ventricular pace would occur during the right ventricle's physiological refractory period and cause no harm.

As mentioned above, certain patients may experience some cardiac resynchronization from the pacing of only one ventricle and/or one atrium with a conventional bradycardia pacing mode. It may be desirable, however, to pace a single atrium or ventricle in accordance with a pacing mode based upon senses from the contralateral chamber. This mode, termed synchronized chamber-only pacing, involves pacing only the synchronized chamber based upon senses from the rate chamber. One way to implement synchronized chamber-only pacing is to pseudo-pace the rate chamber whenever the synchronized chamber is paced before the rate chamber is paced, such that the pseudo-pace inhibits a rate chamber pace and resets any rate chamber escape intervals. Such pseudo-pacing can be combined with the offset synchronized pacing mode using a negative offset to pace the synchronized chamber before the rate chamber and thus pseudo-pace the rate chamber, which inhibits the real scheduled rate chamber pace and resets the rate chamber pacing escape intervals. One advantage of this combination is that sensed events in the rate chamber will inhibit the synchronized chamber-only pacing, which may benefit some patients by preventing pacing that competes with intrinsic activation (i.e., fusion beats). Another advantage of this combination is that rate chamber pacing can provide backup pacing when in a synchronized chamber-only pacing mode, such that when the synchronized chamber pace is prevented, for example to avoid pacing during the chamber vulnerable period following a prior contraction, the rate chamber will not be pseudo-paced and thus will be paced upon expiration of the rate chamber escape interval. Synchronized chamber-only pacing can be combined also with a triggered synchronized pacing mode, in particular with the type in which the synchronized chamber is triggered by a sense in the rate chamber. One advantage of this combination is that sensed events in the rate chamber will trigger the synchronized chamber-only pacing, which may benefit some patients by synchronizing the paced chamber contractions with premature contralateral intrinsic contractions.

An example of synchronized chamber-only pacing is left ventricle-only synchronized pacing where the rate and synchronized chambers are the right and left ventricles, respectively. Left ventricle-only synchronized pacing may be advantageous where the conduction velocities within the ventricles are such that pacing only the left ventricle results in a more coordinated contraction by the ventricles than with conventional right ventricular pacing or biventricular pacing. Left ventricle-only synchronized pacing may be implemented in inhibited demand modes with or without atrial tracking, similar to biventricular pacing. A left ventricular pace is then delivered upon expiration of the AVI escape interval or expiration of the LRL escape interval, with left ventricular pacing inhibited by a right ventricular sense that restarts the LRL escape interval and stops the AVI escape interval.

In the synchronized modes described above, the rate chamber is synchronously paced with a mode based upon detected intrinsic activity in the rate chamber, thus protecting the rate chamber against paces being delivered during the vulnerable period. In order to provide similar protection to a synchronized chamber or synchronized pacing site, a synchronized chamber protection period (SCPP) may be provided. (In the case of multi-site synchronized pacing, a similar synchronized site protection period may be provided for each synchronized site.) The SCPP is a programmed interval which is initiated by sense or pace occurring in the synchronized chamber during which paces to the synchronized chamber are inhibited. For example, if the right ventricle is the rate chamber and the left ventricle is the synchronized chamber, a left ventricular protection period LVPP is triggered by a left ventricular sense which inhibits a left ventricular pace which would otherwise occur before the escape interval expires. The SCPP may be adjusted dynamically as a function of heart rate and may be different depending upon whether it was initiated by a sense or a pace. The SCPP provides a means to inhibit pacing of the synchronized chamber when a pace might be delivered during the vulnerable period or when it might compromise pumping efficiency by pacing the chamber too close to an intrinsic beat. In the case of a triggered mode where a synchronized chamber sense triggers a pace to the synchronized chamber, the pacing mode may be programmed to ignore the SCPP during the triggered pace. Alternatively, the mode may be programmed such that the SCPP starts only after a specified delay from the triggering event, which allows triggered pacing but prevents pacing during the vulnerable period.

In the case of synchronized chamber-only synchronized pacing, a synchronized chamber pace may be inhibited if a synchronized chamber sense occurs within a protection period prior to expiration of the rate chamber escape interval. Since the synchronized chamber pace is inhibited by the protection period, the rate chamber is not pseudo-paced and, if no intrinsic activity is sensed in the rate chamber, it will be paced upon expiration of the rate chamber escape intervals. The rate chamber pace in this situation may thus be termed a safety pace. For example, in left ventricle-only synchronized pacing, a right ventricular safety pace is delivered if the left ventricular pace is inhibited by the left ventricular protection period and no right ventricular sense has occurred.

As noted above, synchronized pacing may be applied to multiple sites in the same or different chambers. The synchronized pacing modes described above may be implemented in a multi-site configuration by designating one sensing/pacing channel as the rate channel for sensing/pacing a rate site, and designating the other sensing/pacing channels in either the same or the contralateral chamber as synchronized channels for sensing/pacing one or more synchronized sites. Pacing and sensing in the rate channel then follows rate chamber timing rules, while pacing and sensing in the synchronized channels follows synchronized chamber timing rules as described above. The same or different synchronized pacing modes may be used in each synchronized channel.

4. Intraventricular Interval Display

The present invention relates to a method for displaying electrogram data received via telemetry by an external programmer or similar device from a pacemaker operating in a cardiac resynchronization mode. Such data is displayed in the form of markers representing cardiac events together with interval values indicating the time intervals between such events on an electronic display or print output of an external programmer. In such a pacemaker, one heart chamber is paced through a rate sensing/pacing channel and another site is paced through a synchronized sensing/pacing channel with the pacing mode being based upon senses and paces in the rate channel. Markers representing sensing and pacing events are displayed spaced apart in accordance with their time sequence, where each marker indicates whether the event is a sense or a pace and in which channel the event occurred. An interval value is displayed with each rate channel marker indicating the time interval between the event represented by the marker and the preceding rate channel event. In alternate embodiments, an interval value is displayed with each synchronized channel marker indicating the time interval either between the event represented by the marker and a nearest rate channel event or between the event represented by the marker and the nearest preceding rate channel sense or synchronized channel pace.

The invention may be applied to pacemakers in which the rate and synchronized channels are paired ventricular channels, paired atrial channels, or a rate channel and a plurality of synchronized channels. FIGS. 2A through 2D show exemplary embodiments of the invention in which the pacemaker is operated such that the right ventricle is designated the rate chamber and the left ventricle designated the synchronized chamber. Markers representing ventricular events are displayed with associated intraventricular intervals. Only ventricular markers and intervals are shown in these examples, but in a typical implementation, markers and intervals for atrial events could also be shown.

Figure 2A:
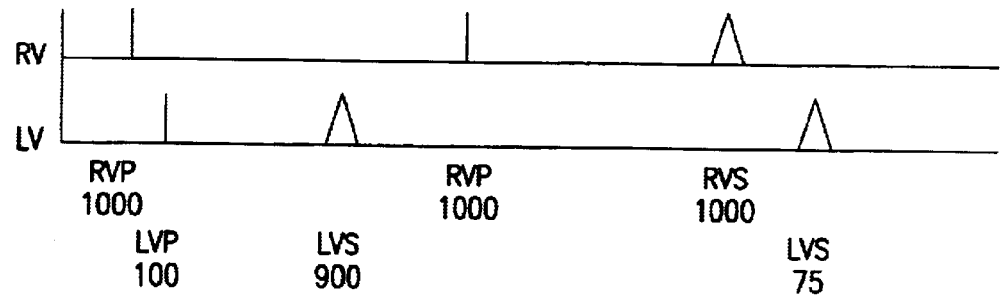
FIGS. 2A through 2D show timelines of events in the right and left ventricular channels of a biventricular pacemaker and a sequence of markers indicating sensing and pacing events and intraventricular intervals.

FIG. 2A shows an embodiment for a pacemaker operating in a biventricular pacing mode. Timelines are displayed representing electrogram data for the right and left ventricular sensing/pacing channels, labeled RV and LV, respectively. Underneath the timelines are two lines of markers output by the display for both ventricular channels. Each marker in the top line represents right ventricular events, and each marker in the bottom line represents left ventricular events. Associated with each marker is an intraventricular interval which indicates the time interval between the event represented by the marker and another ventricular event. The interval displayed with each right and left ventricular marker is the interval from the previous right ventricular event.

Figure 2B:
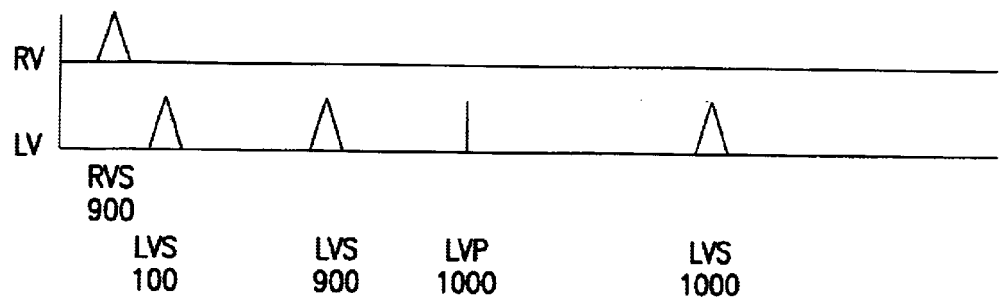

FIG. 2B shows an example of a display for a pacemaker operating in a left ventricular-only pacing mode based upon right ventricular senses. The interval displayed with each marker in this case is the interval from the nearest right ventricular sense or left ventricular pace. Thus, if there is no right ventricular sensing present, the interval displayed with each left ventricular marker is the interval from the previous left ventricular pace.

Figure 2C:
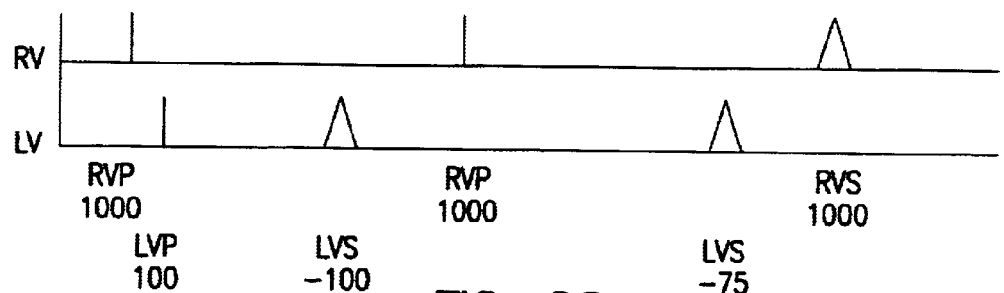

FIG. 2C shows another scheme in which the interval displayed with each left ventricular marker is the interval between the left ventricular event and the nearest right ventricular event. The nearest right ventricular event may precede or follow the left ventricular event as indicated by a positive or negative interval value, respectively. The interval displayed with the right ventricular marker in this embodiment is the interval from the preceding right ventricular event.

Figure 2D:
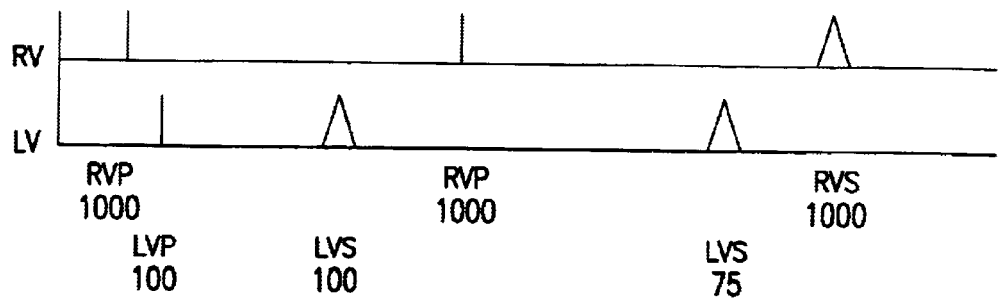

FIG. 2D is an alternative approach in which the interval displayed with each left ventricular marker is the absolute value of the interval between the left ventricular event and the nearest right ventricular event which may precede or follow the left ventricular event, and the interval is displayed in alignment with the marker representing the later of either the left ventricular or right ventricular event. The interval displayed with the right ventricular marker is again the interval from the preceding right ventricular event.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for displaying electrogram data collected by a pacemaker where one heart chamber is paced through a rate sensing/pacing channel and another site in the same or contralateral chamber is paced through a synchronized sensing/pacing channel with the pacing mode being based upon senses and paces in the rate channel, comprising:

displaying markers representing sensing and pacing events spaced apart in accordance with their time sequence, wherein each marker indicates whether the event is a sense or a pace and in which channel the event occurred;

displaying an interval value with each rate channel marker indicating the time interval between the event represented by the marker and the preceding rate channel event; and, displaying an interval value with each synchronized channel marker indicating the time interval between the event represented by the marker and a nearest rate channel event.

2. The method of claim 1 wherein the rate and synchronized channels are right and left ventricular channels.

3. The method of claim 1 wherein the rate and synchronized channels are right and left atrial channels.

4. The method of claim 1 wherein the pacemaker is operated with a plurality of synchronized channels and further comprising displaying markers for each such channel.

5. The method of claim 1 wherein the displayed interval value with each synchronized channel marker indicates the time interval between the event represented by the marker and the nearest preceding rate channel event.

6. The method of claim 1 wherein the displayed interval value with each synchronized channel marker indicates the time interval between the event represented by the marker and the nearest rate channel event which may follow or precede the synchronized channel event as indicated by a negative or positive interval value, respectively.

7. The method of claim 1 wherein the displayed interval value with each synchronized channel marker indicates the absolute value of the time interval between the event represented by the marker and the nearest rate channel event which may precede or follow the synchronized channel event, and the synchronized channel interval is displayed in alignment with the marker representing the later of either the synchronized channel or rate channel event.

8. A method for displaying electrogram data collected by a pacemaker where one heart chamber is paced through a rate sensing/pacing channel and another site in the same or contralateral chamber is paced through a synchronized sensing/pacing channel with the pacing mode being based upon senses and paces in the rate channel, comprising:

displaying markers representing sensing and pacing events spaced in accordance with their time sequence, wherein each marker indicates whether the event is a sense or a pace and in which channel the event occurred;

displaying an interval value with each rate channel marker indicating the time interval between the event represented by the marker and the preceding rate channel event; and, displaying an interval value with each synchronized channel marker indicating the time interval between the event represented by the marker and either the preceding rate channel sense or synchronized channel pace, whichever is nearest.

9. The method of claim 8 wherein the rate and synchronized channels are right and left ventricular channels.

10. The method of claim 8 wherein the rate and synchronized channels are right and left atrial channels.

11. The method of claim 8 wherein the pacemaker is operated with a plurality of synchronized channels and further comprising displaying markers for each such channel.

12. The method of claim 8 wherein the displayed interval value with each synchronized channel marker indicates the time interval between the event represented by the marker and the nearest preceding rate channel event.

13. The method of claim 8 wherein the displayed interval value with each synchronized channel sense marker indicates the time interval between the event represented by the marker and the nearest rate channel sense event or synchronized channel pace event which may follow or precede the synchronized channel sense event as indicated by a negative or positive interval value, respectively.

14. The method of claim 8 wherein the displayed interval value with each synchronized channel sense marker indicates the time interval between the event represented by the marker and the nearest rate channel sense event or synchronized channel pace event which may precede or follow the synchronized channel sense event, and the synchronized channel sense interval is displayed with the marker representing the later of either the synchronized channel or rate channel event.

* * * * *

UNITED STATES PATENT AND TRADEMARK OFFICE
CERTIFICATE OF CORRECTION

PATENT NO.        : 6,957,100 B2                                            Page 1 of 1
APPLICATION NO.   : 09/748724
DATED             : October 18, 2005
INVENTOR(S)       : Vanderlinde et al.

It is certified that error appears in the above-identified patent and that said Letters Patent is hereby corrected as shown below:

On the face page, in field (75), under "Inventors", in column 1, lines 3-4, delete "white Bear Lake, MN (US)" and Insert -- LEEMVELDSTRAAT 40 A 3090 OVERIJSE BELGIUM --, therefor.

On the face page, in field (56), under "Foreign Patent Documents", in column 2, line 4, delete "WO-95/092029" and insert -- WO-95/09029--, therefor.

On the face page, in field (56), under "Foreign Patent Documents", in column 2, line 4, after "4/1995" insert -- A61N --.

On the face page, in field (56), under "Foreign Patent Documents", in column 2, line 5, delete "WO-9711745" and insert -- WO-97/11745--, therefor.

On page 2, In field (56), under "Other Publications", in column 1, line 55, below "5,365,932" insert -- 5,372,607 * 12/1994 Stone et al.   607/30--.

On page 3, In field (56), under "Other Publications", in column 1, line 43, below "6,081,747" insert -- 6,081,748 * 6/2000 Struble et al.   607/9--.

On page 3, In field (56), under "Other Publications", in column 1, line 49, below "6,122,545" insert -- 6,128,529 * 10/2000   Esler         607/4
                    6,129,745 * 10/2000   Sun et al.    607/27 --.

On page 3, In field (56), under "Other Publications", in column 1, line 60, below "6,353,759" insert -- 6,353,761 * 3/2002 Conley et al. 607/28--.

Signed and Sealed this

Twenty-third Day of January, 2007

JON W. DUDAS
*Director of the United States Patent and Trademark Office*